United States Patent
Takaoka (10) Patent No.: US 11,739,376 B2
(45) Date of Patent: Aug. 29, 2023

(54) METHOD AND DEVICE FOR TESTING TARGET NUCLEIC ACID

(71) Applicant: SHIMADZU CORPORATION, Kyoto (JP)

(72) Inventor: Naoko Takaoka, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 144 days.

(21) Appl. No.: 17/024,225

(22) Filed: Sep. 17, 2020

(65) Prior Publication Data

US 2021/0087608 A1  Mar. 25, 2021

(30) Foreign Application Priority Data

Sep. 20, 2019 (JP) ................... 2019-171735

(51) Int. Cl.
*C12Q 1/686* (2018.01)
*C12Q 1/6806* (2018.01)
*G01N 21/39* (2006.01)

(52) U.S. Cl.
CPC ......... *C12Q 1/686* (2013.01); *C12Q 1/6806* (2013.01); *C12Q 2560/00* (2013.01); *C12Q 2600/16* (2013.01); *G01N 2021/392* (2013.01)

(58) Field of Classification Search
CPC ... C12Q 1/686; C12Q 1/705; C12Q 2600/166
See application file for complete search history.

(56) References Cited

U.S. PATENT DOCUMENTS

| 2013/0022963 A1* | 1/2013 | Exner ............... C12Q 1/70 435/6.12 |
| 2015/0275294 A1* | 10/2015 | Leutenegger ........ C12Q 1/686 435/6.12 |
| 2018/0087106 A1 | 3/2018 | Shimizu et al. |

FOREIGN PATENT DOCUMENTS

| JP | 2004-507248 A | 3/2004 |
| JP | WO2016/059798 A1 | 4/2016 |
| WO | WO 02/16648 A2 | 2/2002 |

OTHER PUBLICATIONS

Mary C. Longo et al., "Use of uracil DNA glycosylase to control carry-over contamination in polymerase chain reactions", Gene. 93 (1990), pp. 125-128.

Japanese Office Action dated Nov. 15, 2022 in Japanese Patent Application No. 2019-171735 (with unedited computer-generated English Translation), 5 pages.

* cited by examiner

*Primary Examiner* — Teresa E Strzelecka
(74) *Attorney, Agent, or Firm* — Oblon, McClelland, Maier & Neustadt, L.L.P.

(57) ABSTRACT

A method for testing target nucleic acid includes the steps from (1) through (5) below: (1) mixing a specimen containing target nucleic acid with positive control nucleic acid to obtain a specimen mixture of the specimen and the positive control nucleic acid; (2) mixing the specimen mixture with a PCR buffer solution containing a surfactant to obtain a buffer solution mixture; (3) adding a portion of the buffer mixture to a solid composition for PCR control containing DNA polymerase, positive control nucleic acid, and PCR reaction control nucleic acid; (4) adding a portion of the buffer mixture to a solid composition for PCR reaction containing DNA polymerase and one or more kinds of PCR (Continued)

primer pair; and (5) detecting a PCR product generated as a result of the steps (3) and (4).

33 Claims, 3 Drawing Sheets

FIG. 1

| PATHOGENS | THE NUMBER OF SPECIMENS | QUANTITATIVE PCR (COPIES/mL) | TUBE STRIP (Cq VALUE) |
|---|---|---|---|
| HSV-1 | 14 | $2.48 \times 10^4 \sim 2.55 \times 10^5$ | $36.13 \sim 30.05$ |
| HSV-2 | 2 | $6.38 \times 10^3 \sim 5.32 \times 10^4$ | $31.74 \sim 30.53$ |
| VZV | 35 | $1.97 \times 10^3 \sim 2.88 \times 10^8$ | $36.06 \sim 18.78$ |
| EBV | 3 | $4.63 \times 10^4 \sim 3.30 \times 10^5$ | $36.06 \sim 26.09$ |
| CMV | 34 | $1.25 \times 10^3 \sim 4.43 \times 10^6$ | $36.61 \sim 24.79$ |
| HHV-6 | 0 | - | - |
| HTLV-1 | 6 | $1.41 \times 10^2 \sim 8.48 \times 10^5$ | $39.72 \sim 32.14$ |
| TREPONEMA PALLIDUM | 1 | $2.34 \times 10^4$ | 27.93 |
| TOXOPLASMA | 2 | $8.39 \times 10^4 \sim 1.12 \times 10^6$ | $22.20 \sim 30.02$ |

| DIAGNOSIS | THE NUMBER OF CASES | QUANTITATIVE PCR (COPIES/mL) | TUBE STRIP (Cq VALUE) |
|---|---|---|---|
| IDIOPATHIC UVEITIS | 35 | NOT DETECTED | NOT DETECTED |
| ACUTE ANTERIOR UVEITIS | 2 | NOT DETECTED | NOT DETECTED |
| OCCLUSION OF RETINAL VEIN | 2 | NOT DETECTED | NOT DETECTED |
| BULLOUS KERATOPATHY | 2 | NOT DETECTED | NOT DETECTED |
| PRIMARY OPEN-ANGLE GLAUCOMA | 2 | NOT DETECTED | NOT DETECTED |
| SARCOIDOSIS | 1 | NOT DETECTED | NOT DETECTED |
| VOGT-KOYANAGI-HARADA SYNDROME | 1 | NOT DETECTED | NOT DETECTED |
| BEHÇET'S DISEASE | 1 | NOT DETECTED | NOT DETECTED |
| CHRONIC ANGLE-CLOSURE GLAUCOMA | 1 | NOT DETECTED | NOT DETECTED |
| DIABETIC IRIDOCYLITIS | 1 | NOT DETECTED | NOT DETECTED |
| OTHERS | 4 | NOT DETECTED | NOT DETECTED |

FIG. 4

METHOD AND DEVICE FOR TESTING TARGET NUCLEIC ACID

CROSS-REFERENCE TO RELATED APPLICATIONS

The present application is based upon and claims the benefit of priority to Japanese Patent Application No. 2019-171735, filed Sep. 20, 2019, the entire contents of which are incorporated herein by reference.

BACKGROUND OF THE INVENTION

1. Field of the Invention

The present invention relates to a method for detecting nucleic acid to be a target (hereinafter, may be referred to as target nucleic acid) from a specimen[analyte?] containing target nucleic acid and a kit for performing the method. More specifically, the invention relates to a method including: mixing positive control nucleic acid in a container for a specimen containing target nucleic acid; and detecting the target nucleic acid in the specimen, and a kit used for the method.

2. Description of the Related Art

Techniques related to amplification and detection of nucleic acid are widely used in various fields, such as diagnosis of infectious diseases, nucleic acid testing of crops, and genetic diagnosis. Various methods are used for amplifying and detecting nucleic acid.

Such a method for amplifying nucleic acid includes, in addition to representative PCR methods using polymerase chain reaction (hereinafter, may be referred to as PCR), transcription-reverse transcription concerted reaction (hereinafter, may be referred to as TRC) methods, transcription mediated amplification (hereinafter, may be referred to as TMA) methods, nucleic acid sequence-based amplification (hereinafter, may be referred to as NASBA) methods, loop-mediated isothermal amplification (hereinafter, may be referred to as LAMP) methods, SMart amplification process (hereinafter, may be referred to as SMAP) methods, isothermal and chimeric primer-initiated amplification of nucleic acids (hereinafter, may be referred to as ICAN) methods, and the like.

An example of such diagnosis of infectious diseases using a PCR method includes diagnosis of uveitis. Uveitis is a generic term for diseases causing inflammation in the eye, and in severe cases, visual impairment, such as blindness, occurs at a high rate. Uveitis is classified into noninfectious uveitis and infectious uveitis caused by pathogens. Noninfectious uveitis is subjected to medication with immunosuppressants, whereas infectious uveitis has to be treated with a drug effective for the causative pathogen.

However, differentiation of infectious uveitis from non-infectious uveitis is sometimes difficult only by clinical findings and there are cases resulting in more serious symptoms due to delay in diagnosis or inappropriate treatment. Early confirmation of the presence of a pathogen and identification of the pathogen in uveitis is thus important for selecting an appropriate treatment method and preventing the symptom from being more serious.

Examples of the pathogens causing infectious uveitis include viruses, bacteria, fungi, protozoans, and the like, and infectious uveitis caused by virus most frequently occurs. Examples of the causative virus include: Herpesvirus, such as herpes simplex viruses (HSV) type 1 and type 2, varicella zoster virus (VZV), and cytomegalovirus (CMV); human T cell leukemia virus type 1 (HTLV-1); and the like. Identification of the infective particle is important information for diagnosis and treatment of infectious uveitis. Accordingly, the vitreous body taken from the eye, or the like has to be used as a specimen to identify the infecting virus in the affected area of the eye, aqueous humor collected from the anterior chamber.

The anterior chamber is a space between the cornea and the crystalline lens and the aqueous humor filling the space is used as a specimen for genetic testing by PCR to identify the pathogen. However, the amount of the collected aqueous humor of the anterior chamber is generally 100 µL or less and the amount of the specimen is sometimes insufficient to detect a plurality of pathogens.

In infectious uveitis, major examples of the causative pathogens include nine types of herpes simplex viruses type 1 (HSV-1) and type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum* as a bacterium, and toxoplasma as a protozoan.

For individual detection of these pathogens, a PCR reagent, a PCR primer, and the like have to be prepared for each pathogen while an increase in the number of detection objects causes a higher possibility of human error, such as placing a wrong reagent, and a risk of giving a wrong detection result.

Other than human errors, a false positive or the like sometimes occurs due to mixing (contamination) of an amplification product of a previous nucleic acid amplification reaction in a container for a new nucleic acid amplification reaction. Disclosed methods for preventing such contamination include a dUTP/UDG contamination removal method (Gene, Vol. 93 (1), 125-128 (1990)) and a method developed by improving the dUTP/UDG contamination removal method (JP 2004-507248 A).

In addition, amplification and detection of nucleic acid sometimes result in negative (false negative) for some reason although the nucleic acid is actually positive. Since such a result of false negative means that the nucleic acid to be primarily detected is not detected, a method for preventing false negative as far as possible is proposed (e.g., WO 2016/059798).

SUMMARY

It is an object of the present invention to provide a detection method allowing simultaneous and rapid detection a plurality of pathogens even with small amounts of specimens and a kit for performing the method. It is another object of the present invention to provide a detection method that avoids a human error in operation of detecting pathogens by employing a simplified detection procedure to allow reduction of the probability of false negatives and a kit for performing the method.

That is, the present invention relates to a method for testing target nucleic acid including the steps from (1) through (5) below:

(1) mixing a specimen containing target nucleic acid with positive control nucleic acid to obtain a specimen mixture of the specimen and the positive control nucleic acid;

(2) mixing the specimen mixture with a PCR buffer solution containing a surfactant to obtain a buffer solution mixture;

(3) adding a portion of the buffer mixture to a solid composition for PCR control containing DNA polymerase, positive control nucleic acid, and PCR reaction control nucleic acid;

(4) adding a portion of the buffer mixture to a solid composition for PCR reaction containing DNA polymerase and one or more kinds of PCR primer pair; and (5) detecting a PCR product generated as a result of the steps (3) and (4).

The present invention also relates to a kit for testing target nucleic acid including (1) through (4) below:

(1) a specimen collection container provided with positive control nucleic acid;

(2) a PCR reaction solution container provided with a PCR buffer solution containing a surfactant;

(3) a PCR reaction control container provided with a solid composition for PCR control containing DNA polymerase, positive control nucleic acid, and PCR reaction control nucleic acid; and (4) at least one or more PCR reaction containers provided with a solid composition for PCR reaction containing DNA polymerase and one or more kinds of PCR primer pair.

The present invention is capable of providing a detection method allowing simultaneous and rapid detection of a plurality of pathogens even with small amounts of specimens containing target nucleic acid (e.g., aqueous humor of the anterior chamber) and a kit for performing the method. The present invention is also capable of providing a detection method that avoids a human error in operation of detecting pathogens by a simplified detection procedure to particularly allow reduction of the frequency of false positives and a kit for performing the method.

DETAILED DESCRIPTION OF THE PREFERRED EMBODIMENTS

A method of the present invention includes mixing a specimen containing target nucleic acid with positive control nucleic acid to obtain a specimen mixture of the specimen and the positive control nucleic acid (hereinafter, may be referred to as a step (1)).

The target nucleic acid herein means nucleic acid subjected to detection or quantification in a test sample and means nucleic acid in a region amplified by nucleic acid amplification reaction using a PCR primer pair in a procedure described later.

The target nucleic acid may be appropriately selected in accordance with the purpose, such as disease diagnosis and assessment of disease incidence risk, and examples of the target nucleic acid include the following genes:

1. genes (including non-coding regions) and the like associated with the cause or aggravation of disease or a portion thereof, or a transcription product thereof;

2. genes (including non-coding regions) and the like abnormally expressed by disease incidence or a portion thereof, or a transcription product thereof; and 3. genes (including non-coding regions) and the like associated with disease incidence risk or a portion thereof, or a transcription product thereof.

Specific examples of the above genes and the like include genes and the like of viruses, bacteria, fungi, and protozoans that may be a cause of disease and the like.

Such a virus includes DNA viruses and RNA viruses. Examples of such a DNA virus include, but not limited to, herpes simplex virus type 1 (hereinafter, may be referred to as HSV-1) and type 2 (hereinafter, may be referred to as HSV-2), varicella zoster virus (hereinafter, may be referred to as VZV), Epstein-Barr virus (hereinafter, may be referred to as EBV), human herpesvirus type 6 (hereinafter, may be referred to as HHV-6), cytomegalovirus (hereinafter, may be referred to as CMV), and the like. Examples of such a RNA virus include, but not limited to, human T cell leukemia virus type 1 (hereinafter, may be referred to as HTLV-1) and the like. Examples of such a bacterium as a detection object include, but not limited to, *Treponema pallidum* and the like, and examples of such a protozoan as a detection object include, but not limited to, toxoplasma and the like.

It should be noted that the specimen herein contains the above target nucleic acid and that the species from which the specimen is collected may be different from or same as the species from which the target nucleic acid is derived. An example of the case of different species includes a case for checking whether a mammal is infected with a pathogenic microorganism where a specific nucleic acid in the pathogenic microorganism is used as the target nucleic acid and a specimen is collected from the mammal. An example of the case of the same species includes a case for checking whether a mammal is affected by a disease where a specific nucleic acid in a mammalian gene associated with the disease is used as the target nucleic acid and a specimen is collected from the mammal.

Specific examples of the specimen include a solid sample, a mucous sample, or a humoral sample obtained from an ocular tissue. For example, to diagnose infection with a pathogen in uveitis, aqueous humor of the anterior chamber or the vitreous body is preferably used. The aqueous humor is generally collected approximately from 50 to 100 µL. The present invention allows detection of infection with a microorganism using from 12 to 20 µL of the aqueous humor or the vitreous body while the invention is also capable of detecting even with less than 12 µL depending on the number of microorganisms subjected to the measurement.

The positive control nucleic acid mixed in the step (1) becomes a positive control for the target nucleic acid. The specimen and the positive control are mixed in the step (1) to perform the later steps described below, thereby checking that a PCR primer pair performs an intended function to correctly carry out nucleic acid amplification reaction and a probe for the target nucleic acid performs an intended function.

The positive control nucleic acid may be extracted and amplified in advance from the species from which the specimen is derived or the species from which the target nucleic acid is derived, or may be separately extracted from different species. The positive control nucleic acid may be artificially synthesized nucleic acid.

The positive control nucleic acid is preferably nucleic acid contained in the species from which the specimen is collected, and from the perspective of the above effects, more preferably a housekeeping gene.

Examples of the housekeeping gene include a TATA-binding protein (hereinafter, may be referred to as TBP) gene, a glyceraldehyde-3-phosphate dehydrogenase (hereinafter, may be referred to as GAPDH) gene, a β-actin gene, a β2-microglobulin gene, hypoxanthine phosphoribosyl transferase 1 (hereinafter, may be referred to as HPRT 1), a 18S rRNA gene, a 5-aminolevulinate synthase (hereinafter, may be referred to as ALAS) gene, a β-globin gene, a glucose-6-phosphate dehydrogenase (hereinafter, may be referred to as G6PD) gene, a β-glucuronidase (hereinafter, may be referred to as GUSB) gene, an importin 8 (hereinafter, may be referred to as IPO8) gene, a porphobilinogen deaminase (hereinafter, may be referred to as PBGD) gene, a phosphoglycerate kinase 1 (hereinafter, may be referred to as PGK1) gene, a peptidylprolyl isomerase A (hereinafter, may be referred to as PPIA) gene, a ribosomal protein L13a (hereinafter, may be referred to as RPL13A) gene, a ribosomal protein large PO (hereinafter, may be referred to as RPLPO) gene, a succinate dehydrogenase subunit A (hereinafter, may be referred to as SDHA) gene, a transferrin receptor (hereinafter, may be referred to as TFRC) gene, a 3-monooxygenase/tryptophan 5-monooxygenase activation protein, zeta (hereinafter, may be referred to as YWHAZ) gene, and the like.

The specimen mixture obtained in the step (1) is mixed with a PCR buffer solution containing a surfactant to obtain a buffer solution mixture (hereinafter, may be referred to as a step (2)).

The specimen containing target nucleic acid, such as aqueous humor of the anterior chamber and the vitreous body, is considered to be mixed with the PCR buffer solution containing a surfactant to promote dissolution of the target nucleic acid during PCR. The surfactant contained in the PCR buffer solution may be selected from an anionic surfactant, a cationic surfactant, an amphoteric surfactant, and a nonionic surfactant. The surfactant is preferably a nonionic surfactant and is preferably from 0.05% to 5% (w/v) when mixed with the specimen.

The PCR buffer solution preferably contains KCl, $MgCl_2$, and deoxyribonucleotide 5'-triphosphate (dNTP) mix from the perspective of solubility of the target nucleic acid. It should be noted that the dNTP mix is an aqueous solution obtained by mixing deoxyadenosine triphosphate (hereinafter, may be referred to as dATP), deoxyguanosine triphosphate (hereinafter, may be referred to as dGTP), deoxycytidine triphosphate (hereinafter, may be referred to as dCTP), and deoxythymidine triphosphate (hereinafter, may be referred to as dTTP) with a predetermined concentration in advance. The PCR buffer solution is preferably tris-hydrochloric acid from the perspective of solubility of the target nucleic acid. The concentrations of dNTP, $MgCl_2$, KCl, and the buffer solution may be appropriately set according to the kind of specimen, the target nucleic acid, and the PCR primer pair used in later step described below. For example, for the specimen of aqueous humor of the anterior chamber or the vitreous body, it is preferred to use approximately 1.5 mM of $MgCl_2$, approximately 35 mM of KCl, approximately 200 μM of dNTP, and approximately 10 mM of tris-hydrochloric acid.

The PCR buffer solution contains substances bonded to PCR inhibitors of a negatively charged biologically derived substance adsorbing to DNA polymerase (e.g., a kind of sugar, a dye, etc.) and a positively charged biologically derived substance adsorbing to DNA (e.g., a kind of protein, etc.) to neutralize PCR inhibitory effect of the negatively charged substance and the positively charged substance. As the PCR buffer solution, it is possible to use a gene amplification reagent Ampdirect® (Shimadzu Corp.) or Ampdirect Plus® (Shimadzu Corp.). Allowing omission of DNA purification process, such as solid phase extraction and liquid-liquid extraction, and thus not having to dispose the liquid, such a gene amplification reagent is preferably used from the perspective of performing PCR reaction and the like with a smaller amount of sample.

A portion of the buffer solution mixture obtained in the step (2) is added to a solid composition for PCR control containing DNA polymerase, positive control nucleic acid, and PCR reaction control nucleic acid (hereinafter, may be referred to as a step (3)).

The positive control nucleic acid used in the step (3) may be same or different from the positive control nucleic acid added in the step (1), and from the perspective of convenience of the method, the same nucleic acid is preferably used. Specific examples of the positive control nucleic acid used in the step (3) include those same as the above examples.

The PCR reaction control nucleic acid exhibiting a positive amplification curve is an index representing that the analysis is correctly performed, that is, the specimen is correctly added to a solid composition for PCR reaction containing DNA polymerase and one or more kinds of PCR primer pair described later.

The PCR reaction control nucleic acid may be extracted and amplified in advance from the species from which the specimen is derived or the species from which the target nucleic acid is derived, or may be separately extracted from different species. The PCR reaction control nucleic acid may be artificially synthesized nucleic acid.

The PCR reaction control nucleic acid is preferably nucleic acid contained in the species from which the specimen is collected and more preferably a housekeeping gene from the perspective of the above effects.

Examples of the housekeeping gene include nucleic acids same as those for the positive control nucleic acid while nucleic acid different from the positive control nucleic acid is preferably used from the perspective of checking that the specimen is correctly added to the solid composition for PCR reaction.

From the perspective of detection precision, the combination of the positive control nucleic acid and the PCR reaction control nucleic acid is preferably a combination of GAPDH and TBP. GAPDH is commonly expressed as a housekeeping gene in a certain amount in many tissues and cells and is used as a positive control to check the progress of PCR. TBP is a general transcription factor bonded to a DNA sequence called as a TATA box and reflects the number of cells and thus is used as a PCR reaction control to check that the cells are collected and contained in the specimen.

The positive control nucleic acid of the present invention is also useful for quantification (absolute quantification or relative quantification) of the target nucleic acid in the test sample. When the positive control nucleic acid is used for absolute quantification, for example, preparation of a calibration curve based on a result of measuring the positive control nucleic acid with a known concentration allows accurate quantification of the target nucleic acid with an unknown concentration in the test sample. When the positive control nucleic acid is used for relative quantification, for example, the number of cycles for reaching a certain concentration may be compared between a positive control nucleic acid sample and the test sample to calculate a relative concentration difference based on the PCR principle of double amplification in one cycle.

A portion of the buffer solution mixture obtained in the step (2) is added to a solid composition for PCR reaction containing separately prepared DNA polymerase and one or more kinds of PCR primer pair (hereinafter, may be referred to as a step (4)).

The step (4) initiates PCR to amplify the target nucleic acid. The DNA polymerase is thermostable DNA polymerase derived from a thermophilic bacterium and examples of the DNA polymerase include Taq, Tth, KOD, Pfu, and a variant thereof. From the perspective of avoiding nonspecific amplification by the DNA polymerase, hot start DNA polymerase may be used. Examples of the hot start DNA polymerase include DNA polymerase to which an anti-DNA polymerase antibody is bonded or DNA polymerase in which an enzyme active site is thermosensitively and chemically modified, and DNA polymerase to which an anti-DNA polymerase antibody is bonded is preferred.

From the perspective of simultaneous detection of a plurality of target nucleic acids, a preferred method includes: preparing two or more solid compositions for PCR reaction containing one or more kinds of PCR primer pair; and adding a portion of the buffer solution mixture obtained in the step (2) to the respective solid compositions for PCR reaction. For example, the buffer solution mixture obtained in the step (2) is added to the plurality of solid compositions for PCR reaction containing the PCR primer pair to allow simultaneous detection of a plurality of target nucleic acids.

Examples of the PCR primer pair used in the step (4) include PCR primer pairs to amplify target gene regions of herpes simplex virus type 1 (HSV-1) or type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum*, and toxoplasma.

Two or more kinds of these PCR primer pairs may be combined and added to the solid composition for PCR reaction. It is thus possible to detect two or more kinds of target nucleic acid with one solid composition for PCR reaction. From the perspective of rapid detection, a preferably used solid composition for PCR reaction is obtained by combining two or more kinds of PCR primer pair.

As a method for using a smaller amount of the specimen to simultaneously amplify a plurality of target genes, multiplex PCR is proposed (Sugita S, et al. Br J Ophthalmol. 2008; 92: 928-932. and Sugita S, et al. Ophthalmology. 2013; 120: 1761-1768.). The multiplex PCR is a method for simultaneously amplifying a plurality of gene regions using a plurality of PCR primer pairs in one PCR reaction system. This method has an advantage of, in addition to use of a smaller amount of the specimen, simultaneous detection of a plurality of pathogenic microorganisms. In this method, however, the nucleic acid has to be extracted from the specimen before performing PCR. In the multiplex PCR, the primers to be used have to be set and the reaction conditions have to be investigated to satisfactorily proceed with amplification of the target gene regions by the respective PCR primer pairs in one PCR reaction system.

Examples of the PCR primer pair include combinations of (i) HSV-1 detecting primer pair and VZV detecting primer pair, (ii) HSV-2 detecting primer pair and HHV-6 detecting primer pair, (iii) EBV detecting primer pair and CMV detecting primer pair; and (vi) HTLV-1 detecting primer pair and *Treponema pallidum* detecting primer pair. To simultaneously detect three kinds of pathogenic microorganism, three or more kinds of PCR primer pair may be added. The base sequence of each primer may be appropriately designed based on base sequence information in sequence database (GenBank, etc.) of the target nucleic acid.

The solid composition for PCR control and the solid composition for PCR reaction used in the steps (3) and (4) are generally prepared by freeze drying while the preparation method is not limited to freeze drying as long as the activity of the enzyme and the like contained in the solid composition is maintained. The form of a solid composition allows PCR to be started only by adding the buffer solution mixture obtained in the step (2), thereby simplifying the measurement operation. It also simplifies storage before use.

The solid composition for PCR control and the solid composition for PCR reaction in the steps (3) and (4) preferably contain an oligonucleotide probe labeled with one or more kinds of fluorescent dye to fluorescently detect a PCR amplification product from the perspective of detection accuracy. When the solid composition for PCR reaction contains one kind of PCR primer pair, a fluorescent dye may be one kind for real-time measurement as described later. In contrast, when the solid composition for PCR reaction contains two or more kinds of PCR primer pair, two or more kinds of fluorescent dye different from each other has to be used. Examples of the fluorescent dye include 6-carboxyfluorescein (hereinafter, may be referred to as FAM), 6-carboxy-X-rhodamine (hereinafter, may be referred to as ROX), a cyanine-based dye (hereinafter, may be referred to as Cy5), and 4,7,2',4',5',7'-hexachloro-6-carboxyfluorescein (hereinafter, may be referred to as HEX). The base sequence of the oligonucleotide probe may be appropriately designed based on base sequence information in sequence database (GenBank, etc.) of the PCR amplification product.

By adding the buffer solution mixture to the solid composition for PCR reaction described above, the solid composition for PCR reaction is dissolved and thermal cycling is performed to proceed with PCR. The PCR conditions (temperature, time, and the number of cycles) are appropriately set according to the kind of target nucleic acid and the like. When the PCR proceeds and the target nucleic acid is contained in the buffer solution mixture, a positive result is obtained in detecting of a PCR product described later to perform disease diagnosis, assessment of disease incidence risk, and the like.

A PCR product generated as a result of the steps (3) and (4) is detected (hereinafter, may be referred to as a step (5)).

Examples of the method for detecting the PCR product include electrophoresis using agarose gel, detection by a thermal melting curve, fluorescence detection, and the like. From the perspective of rapid detection, a detection method called as real-time measurement is preferred.

The real-time measurement of a PCR product is also called as real-time PCR. In real-time PCR, a PCR amplification product is generally detected by fluorescence. Examples of the fluorescence detection method include a method using an intercalator fluorescent dye and a method using a fluorescently labeled probe. An example of the intercalator fluorescent dye includes SYBR® Green I. The intercalator fluorescent dye is bonded to double-stranded DNA synthesized by the PCR and emits fluorescence by irradiation with excitation light. Measurement of the fluorescence intensity allows measurement of the amount of the generated PCR amplification product.

Examples of the fluorescently labeled probe include a hydrolysis probe, a molecular beacon, a cycling probe, and the like. The hydrolysis probe is oligonucleotide having a 5' end modified with a fluorescent dye and a 3' end modified with a quenching material. Although the hydrolysis probe is specifically hybridized with template DNA in an annealing of PCR, the presence of the quencher on the probe inhibits generation of fluorescence even by irradiation with excitation light. In elongation reaction after that, for example when the hydrolysis probe hybridized with the template DNA is degraded by 5'→3' exonuclease activity of Taq DNA polymerase, the fluorescent dye is removed from the probe and the inhibition of the fluorescence generation by the quencher is released to emit fluorescence. Measurement of the fluorescence intensity allows measurement of the amount of the generated amplification product.

Examples of the fluorescent dye include fluorescent dyes similar to those described above. Examples of the quencher include TAMRA®, Black Hole Quencher (BHQ)® 1, BHQ 2, MGB-Eclipse®, DABCYL, and the like. To distinctively detect two or more kinds of target nucleic acid, two or more kinds of oligonucleotide probe (e.g., hydrolysis probe) labeled with respectively different fluorescent dyes are used for PCR from the perspective of detection accuracy.

For real-time measurement of a PCR product, the amplification curve of the PCR product is monitored using a fluorescent filter corresponding to the fluorescent dye to be used, thereby allowing real-time checking of the progress of PCR. When the fluorescence intensity increases with the number of PCR cycles, the presence of target nucleic acid in the specimen is assessed as positive. In contrast, when the fluorescence intensity does not increase, the presence is assessed as negative. At this point, when the fluorescence intensity of the positive control nucleic acid increases with the number of PCR cycles, the specimen is determined to be correctly contained in the buffer solution mixture and served for the step (4). In addition, when the fluorescence intensity of the PCR reaction control nucleic acid increases with the number of PCR cycles, it is determined that the specimen is correctly served for the step (4) and also the DNA polymerase and the PCR primer pair are normally functioning. The reliability of the assessment that the presence of the target nucleic acid is negative is thus improved.

To efficiently perform the above method, the present invention further provides a kit for testing target nucleic acid including (1) through (4) below:

(1) a specimen collection container provided with positive control nucleic acid;

(2) a PCR reaction solution container provided with a PCR buffer solution containing a surfactant;

(3) a PCR reaction control container provided with a solid composition for PCR control containing DNA polymerase, positive control nucleic acid, and PCR reaction control nucleic acid; and (4) at least one or more PCR reaction containers provided with a solid composition for PCR reaction containing DNA polymerase and one or more kinds of PCR primer pair.

The testing kit allows efficient testing when a very small amount of specimen is collected to test a plurality of target nucleic acids following each step described above.

The testing kit of the present invention includes at least one specimen collection container provided with positive control nucleic acid. The positive control nucleic acid to be contained is as described above. The specimen collection container is not particularly limited in shape, size, and the like, and a preferred material for the specimen collection container is easily handled and excellent in chemical resistance. The preferred material is also excellent in visibility.

A required amount of the specimen containing target nucleic acid is dropped into the specimen collection container to obtain a specimen mixture of the specimen and the positive control nucleic acid. From the perspective of testing the target nucleic acid with a small amount of specimen and suppressing human errors, the number of the specimen collection container is preferably one.

The testing kit of the present invention includes at least one PCR reaction solution container provided with a PCR buffer solution containing a surfactant. The surfactant and the PCR buffer solution are as described above.

By dropping an appropriate amount of the specimen mixture obtained in the specimen collection container into the PCR reaction container, it is possible to obtain the buffer solution mixture. From the perspective of suppressing the complexity of the operation, the number of the PCR reaction container is preferably one.

The testing kit of the present invention includes at least one PCR reaction control container provided with a solid composition for PCR control containing DNA polymerase, positive control nucleic acid, and PCR reaction control nucleic acid. A portion of the buffer solution mixture obtained in the PCR reaction solution container is collected and an appropriate amount of the collected mixture is dropped into the PCR reaction control container to perform thermal cycling as described above and proceed with PCR reaction in the PCR reaction control container, and thus the positive control nucleic acid and the PCR reaction control nucleic acid are amplified.

The DNA polymerase, the positive control nucleic acid, and the PCR reaction control nucleic acid contained in the solid composition for PCR control are as described above. The solid composition for PCR control is also as described above.

The number of the PCR reaction control containers may be one, two, or more. From the perspective of the convenience of the operation, the number of the PCR reaction control container is preferably one. In contrast, from the perspective of increasing the accuracy of PCR reaction results, the number of the PCR reaction control containers is preferably two or more. The number of the PCR reaction control containers is appropriately set according to the number of the kinds of target nucleic acid, the amount of the specimen, and the like. The PCR reaction control container may contain the solid composition for PCR control containing the oligonucleotide probe labeled with one or more kinds of fluorescent dye to fluorescently detect the PCR amplification product.

The testing kit of the present invention includes at least one or more PCR reaction containers provided with a solid composition for PCR reaction containing DNA polymerase and one or more kinds of PCR primer pair. A portion of the buffer solution mixture obtained in the PCR reaction solution container is collected and an appropriate amount of the collected mixture is dropped into the PCR reaction container to perform thermal cycling as described above and proceed with PCR reaction in the PCR reaction container, and when the target nucleic acid is present in the specimen, the target nucleic acid is amplified.

The DNA polymerase and the one or more kinds of PCR primer pair contained in the solid composition for PCR reaction are as described above. The solid composition for PCR reaction is also as described above.

The PCR reaction containers is appropriately set according to the number of the kinds of target nucleic acid, the number of the kinds of PCR primer pair contained in the solid composition for PCR reaction, and the like.

The PCR reaction container may contain the solid composition for PCR reaction containing the oligonucleotide probe labeled with one or more kinds of fluorescent dye to fluorescently detect the PCR amplification product. From the perspective of reducing the amount of the specimen, the solid composition for PCR reaction is preferably used that contains a plurality of PCR primer pairs and/or two or more kinds of fluorescent dye.

The PCR product obtained by the testing kit is subjected to an analysis method, such as electrophoresis, detection by a thermal melting curve, and fluorescence detection, for analysis.

The specimen collection container, the PCR reaction solution container, the PCR reaction control container, and the PCR reaction container may be same or different from each other in material, shape, volume, and the like. A preferred material is easily handled and excellent in chemical resistance. The preferred material is also excellent in visibility. Examples of the material include glass, polypropylene, and the like.

From the perspective of ease of handling, for example, all containers are preferably same in shape, volume, and the like. In addition, from the perspective of suppressing human errors such as omissions of adding the specimen and the respective mixtures, each container is preferably prepared to allow identification with colors, signs, numbers, and the like.

Examples of the respective containers to be used include a tube strip in which a plurality of tubes are coupled, and a tube strip coupled with a well is preferred. The number is generally from two to 12, preferably from two to ten, and more preferably from two to eight.

EXAMPLES

The present invention is described in detail with reference to Examples while the scope of the present invention is not limited to them.

Example 1

Analysis of 97 Cases of Positive Specimens of Infectious Uveitis

As 97 cases of specimens obtained from patients suspected of infectious uveitis, 20 µL of aqueous humor of the anterior chamber or the vitreous body was collected in a specimen collection container containing TBP as positive control nucleic acid to obtain a specimen mixture. The specimen mixture thus obtained was mixed with 180 µL of a PCR buffer solution in a PCR reaction container to obtain a buffer solution mixture. The composition of the PCR buffer solution after mixing was 0.05% (w/v) of a nonionic surfactant, 1.5 mM of $MgCl_2$, 35 mM of KCl, and 200 µM each of dNTP (dATP, dGTP, dCTP, and dTTP). Then, 20 µL of the buffer solution mixture thus obtained was dispensed into a PCR reaction control container provided with the solid composition for PCR control containing GAPDH as positive control nucleic acid, TBP as PCR reaction control nucleic acid, and DNA polymerase and respective PCR reaction containers provided with solid compositions for PCR reaction containing the PCR primer pairs and DNA polymerase. The solid composition for PCR control and the solid compositions for PCR reaction further contained an oligonucleotide probe labeled with a fluorescent dye to fluorescently detect a PCR amplification product different for each container. The combinations of the PCR primer pairs in the PCR reaction containers were as follows:

(i) HSV-1 detecting primer pair and VZV detecting primer pair;
(ii) HSV-2 detecting primer pair and HHV-6 detecting primer pair;
(iii) EBV detecting primer pair and CMV detecting primer pair;
(vi) HTLV-1 detecting primer pair and *Treponema pallidum* detecting primer pair; and
(v) toxoplasma detecting primer pair.

The PCR reaction in each container containing the solid composition for PCR control and the solid compositions for PCR reaction dissolved by the buffer solution mixture was monitored by the hydrolysis probe method using a real-time PCR device (Applied Biosystems 7500 Fast Dx Real-Time PCR device). As the PCR conditions, initial denaturation was performed at 95° C./for 10 seconds and then 45 cycles of PCR at 95° C./for 5 seconds –60° C./for 20 seconds. The presence (positive) or the absence (negative) of a pathogenic microorganism as the target nucleic acid was determined based on the Cq value (the number of cycles where the amplification curve intersects with a threshold line). As a comparison, DNA was purified from each specimen, followed by quantification of the number of copies by the real-time PCR (qPCR) method.

Figure 1:
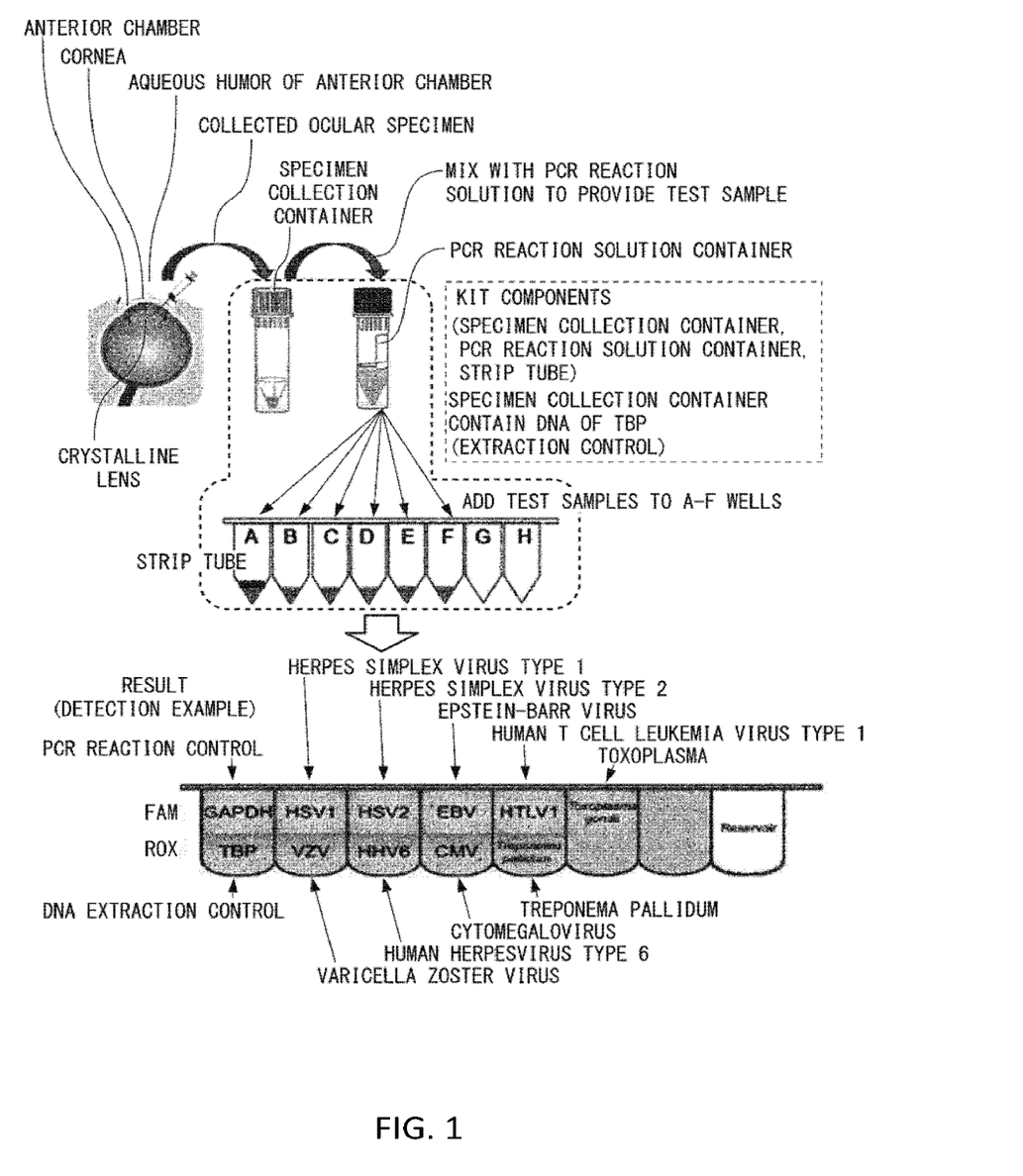
FIG. 1 is a schematic diagram illustrating an embodiment of the present invention.
Figure 2:
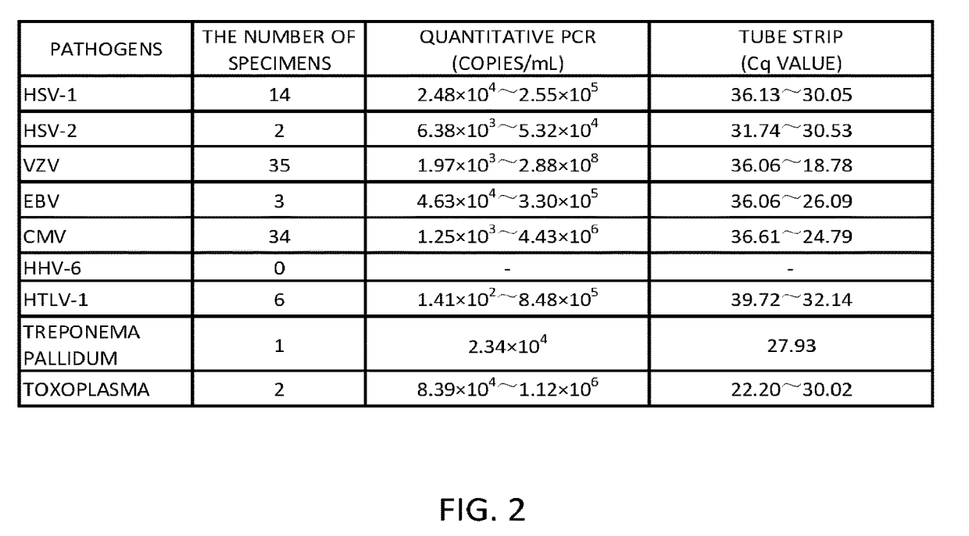
FIG. 2 is a chart illustrating results of analyzing 97 cases of human aqueous humor of the anterior chamber or the human vitreous body suspected of the presence of a pathogen using a method and a kit of the present invention and a quantitative PCR (qPCR) method.
Figure 3:
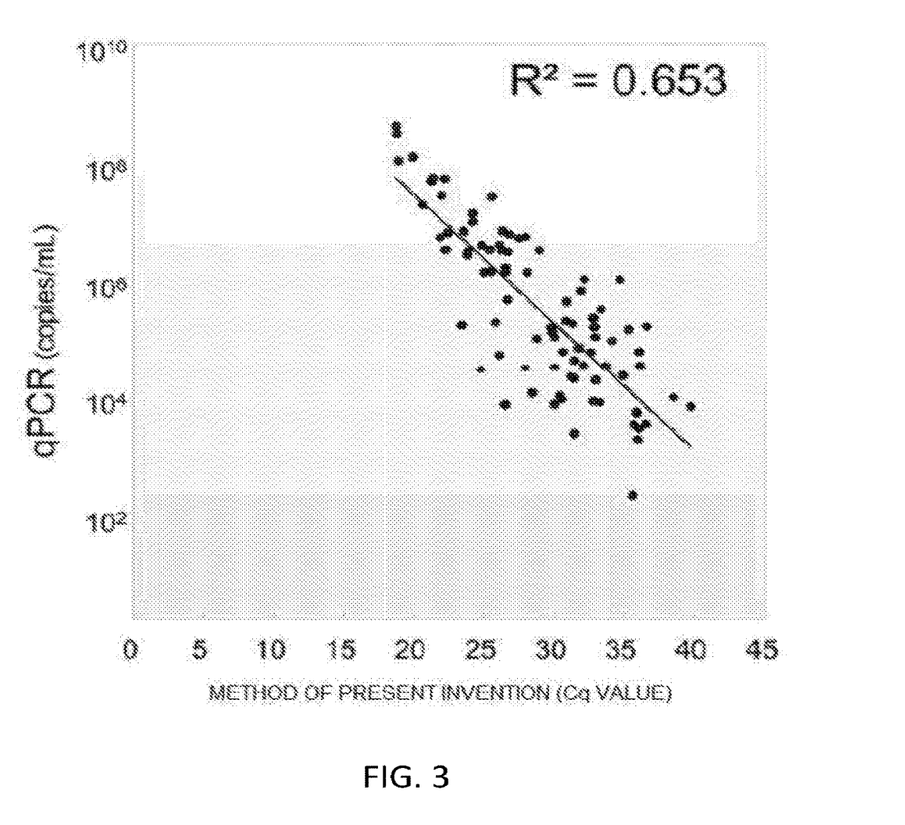
FIG. 3 is a chart illustrating correlation between Cq values obtained using the method and the kit of the present invention and quantitative values (copies/mL) obtained by the quantitative PCR (qPCR) method.

FIG. 2 illustrates the result of comparing the pathogens measured by the method of the present invention with the real-time PCR (qPCR) method. FIG. 3 illustrates correlation between the quantitative values by the real-time PCR (qPCR) method and the Cq values measured by the method of the present invention.

From the results of FIG. 2, the 97 cases of the positive specimens quantified by the real-time PCR (qPCR) method were all positive when measured using the method of the present invention as well. In addition, the results of FIG. 3 show that the quantitative values were correlated with the Cq values. The results of FIG. 3 show that CMV, VZV, HSV-1, HSV-2, HTLV-1, EBV, *Treponema pallidum*, and toxoplasma were identified.

Example 2

Analysis of Specimens Diagnosed as Noninfectious Uveitis

Figure 4:
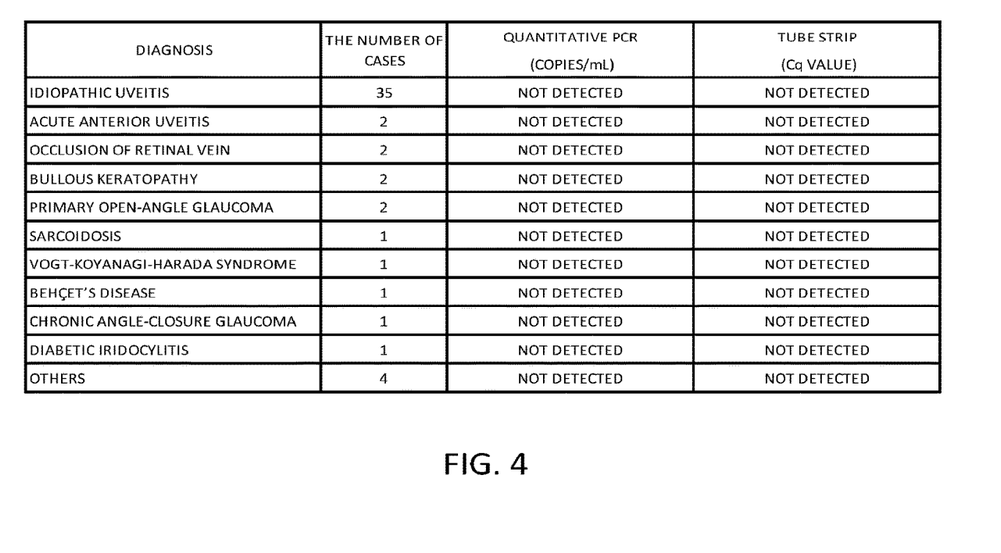
FIG. 4 is a chart illustrating results of analyzing 52 cases of human aqueous humor of the anterior chamber or the human vitreous body diagnosed as noninfectious uveitis using the method and the kit of the present invention and the quantitative PCR (qPCR) method.

FIG. 4 illustrates the result of measuring 52 cases of specimens obtained from patients diagnosed as noninfectious uveitis by the real-time PCR (qPCR) method and the method of the present invention. All specimens were negative by the real-time PCR (qPCR) method and all were negative by the method of the present invention. That is, FIG. 4 shows that the measurement results obtained from both methods coincided with each other.

Aspects

Those skilled in the art would understand that the exemplifying embodiments described above are specific examples of the following aspects.

[1] A method for testing target nucleic acid including the steps from (1) through (5) below:

(1) mixing a specimen containing target nucleic acid with positive control nucleic acid to obtain a specimen mixture of the specimen and the positive control nucleic acid;

(2) mixing the specimen mixture with a PCR buffer solution containing a surfactant to obtain a buffer solution mixture;

(3) adding a portion of the buffer mixture to a solid composition for PCR control containing DNA polymerase, positive control nucleic acid, and PCR reaction control nucleic acid;

(4) adding a portion of the buffer mixture to a solid composition for PCR reaction containing DNA polymerase and one or more kinds of PCR primer pair; and (5) detecting a PCR product generated as a result of the steps (3) and (4).

The invention of [1] above allows simultaneous and rapid detection of a plurality of pathogens even with small amounts of specimens (e.g., aqueous humor of the anterior chamber) containing target nucleic acid. The invention of [1] above is further capable of providing a detection method that avoids a human error in operation of detecting pathogens to particularly allow reduction of the frequency of false positives in a simplified detection procedure.

[2] The method according to [1] above, wherein the specimen is aqueous humor of an anterior chamber or a vitreous body.

[3] The method according to [1] or [2] above, wherein an amount of the specimen is from 12 to 20 μL.

[4] The method according to any one of [1] through [3] above, wherein the specimen includes at least one selected from the group of herpes simplex virus type 1 (HSV-1) and type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), Treponema pallidum, and toxoplasma.

The invention of [2] through [4] above allows simultaneous and rapid detection of pathogens causing infectious uveitis.

[5] The method according to any one of [1] through [4] above, wherein the positive control nucleic acid in the step (1) is a housekeeping gene.

[6] The method according to [5] above, wherein the positive control nucleic acid in the step (1) is TATA-binding protein (TBP).

The invention of [5] and [6] above allows more secure checking that the PCR primer pair performs an intended function to correctly perform the nucleic acid amplification reaction and that the probe for target nucleic acid performs an intended function.

[7] The method according to any one of [1] through [6] above, wherein the surfactant is a nonionic surfactant.

[8] The method according to any one of [1] through [7] above, wherein the PCR buffer solution is a tris buffer solution containing KCl, $MgCl_2$, and dNTP mix (a mixture of dATP, dGTP, dCTP, and dTTP).

[9] The method according to any one of [1] through [8] above, wherein the PCR buffer solution contains substances bonded to PCR inhibitors of a negatively charged biologically derived substance adsorbing to DNA polymerase and a positively charged biologically derived substance adsorbing to DNA to neutralize PCR inhibitory effect of the negatively charged substance and the positively charged substance.

The invention of [7] through [9] above more facilitates dissolution of the target nucleic acid and allows more reduction of the amount of using the specimen.

[10] The method according to any one of [1] through [9] above, wherein at least either one of the positive control nucleic acid and the PCR reaction control nucleic acid in the step (3) is a housekeeping gene.

[11] The method according to any one of [1] through [10] above, wherein the positive control nucleic acid in the step (3) is same as the positive control nucleic acid in the step (1).

[12] The method according to any one of [1] through [11] above, wherein the positive control nucleic acid in the step (3) is TATA-binding protein (TBT) and the PCR reaction control nucleic acid in the step (3) is glyceraldehyde-3-phosphate dehydrogenase (GAPDH).

The invention of [10] through [12] above allows even more secure checking that the PCR primer pair performs an intended function to correctly perform the nucleic acid amplification reaction and that the probe for target nucleic acid performs an intended function.

[13] The method according to any one of [1] through [12] above, wherein the PCR primer pair is a PCR primer pair to detect herpes simplex virus type 1 (HSV-1) or type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), Treponema pallidum, or toxoplasma.

[14] The method according to any one of [1] through [13] above, wherein the two kinds of PCR primer pair is any one of combinations below:

(i) HSV-1 detecting primer pair and VZV detecting primer pair;

(ii) HSV-2 detecting primer pair and HHV-6 detecting primer pair;

(iii) EBV detecting primer pair and CMV detecting primer pair; and (vi) HTLV-1 detecting primer pair and Treponema pallidum detecting primer pair.

The invention of [13] and [14] above allows simultaneous and rapid detection of pathogens causing infectious uveitis.

The method according to any one of [1] through [14] above, wherein the solid composition for PCR control and the solid composition for PCR reaction in the steps (3) and (4) contain an oligonucleotide probe labeled with one or more kinds of fluorescent dye to fluorescently detect a PCR amplification product.

The method according to [15] above, wherein the fluorescent dye is at least one selected from the group of FAM (6-carboxyfluorescein), ROX (6-carboxy-X-rhodamine), Cy5 (cyanine-based dye), and HEX (4,7,2',4',5',7'-hexachloro-6-carboxyfluorescein).

The invention of [15] and [16] above allows obtaining a result with higher detection accuracy.

The method according to any one of [1] through [16] above, wherein the solid composition for PCR control and the solid composition for PCR reaction in the steps (3) and (4) are prepared by freeze drying.

The invention of [17] above simplifies operation for target nucleic acid testing and also simplifies storage before use.

[18] The method according to any one of [1] through [17] above, wherein the PCR product detection in the step (5) is performed by real-time measurement.

The invention of [18] above allows rapid detection of the target nucleic acid.

[19] A kit for testing target nucleic acid including (1) through (4) below:

(1) a specimen collection container provided with positive control nucleic acid;

(2) a PCR reaction solution container provided with a PCR buffer solution containing a surfactant;

(3) a PCR reaction control container provided with a solid composition for PCR control containing DNA polymerase, positive control nucleic acid, and PCR reaction control nucleic acid; and (4) at least one or more PCR reaction containers provided with a solid composition for PCR reaction containing DNA polymerase and one or more kinds of PCR primer pair.

The invention of [19] above is capable of providing a kit for testing target nucleic acid allowing simultaneous and rapid detection of a plurality of pathogens even with small amounts of specimens (e.g., aqueous humor of the anterior chamber) containing target nucleic acid. The invention of [19] above is further capable of providing a kit for testing allowing performance of a detection method that avoids a human error in operation of detecting pathogens to particularly allow reduction of the frequency of false positives in a simplified detection procedure.

[20] The testing kit according to [19] above, wherein the positive control nucleic acid contained in the specimen collection container is a housekeeping gene.

[2] The testing kit according to [19] or [20] above, wherein the positive control nucleic acid contained in the specimen collection container is TATA-binding protein (TBP).

The invention of [20] and [21] above is capable of providing a testing kit in which the PCR primer pair performs an intended function to correctly perform the nucleic acid amplification reaction and that the probe for target nucleic acid performs an intended function.

[22] The testing kit according to [19] above, wherein the surfactant is a nonionic surfactant.

[23] The testing kit according to any one of [19] through [22] above, wherein the PCR buffer solution is a tris buffer solution containing KCl, $MgCl_2$, and dNTP mix (a mixture of dATP, dGTP, dCTP, and dTTP).

[24] The testing kit according to any one of [19] through [23] above, wherein the PCR buffer solution contains substances bonded to PCR inhibitors of a negatively charged biologically derived substance adsorbing to DNA polymerase and a positively charged biologically derived substance adsorbing to DNA to neutralize PCR inhibitory effect of the negatively charged substance and the positively charged substance.

Use of the testing kit of the invention of [22] through [24] above more facilitates dissolution of the target nucleic acid and allows more reduction of the amount of using the specimen.

[25] The testing kit according to any one of [19] through [24] above, wherein at least either one of the positive control nucleic acid and the PCR reaction control nucleic acid contained in the PCR reaction control container is a housekeeping gene.

[26] The testing kit according to any one of [19] through [25] above, wherein the positive control nucleic acid contained in the PCR reaction control container is same as the positive control nucleic acid contained in the specimen collection container.

[27] The method according to any one of [19] through [26] above, wherein the positive control nucleic acid contained in the PCR reaction control container is TATA-binding protein (TBT), and the PCR reaction control nucleic acid contained in the PCR reaction control container is glyceraldehyde-3-phosphate dehydrogenase (GAPDH).

Use of the testing kit of the invention of [25] through [27] above allows even more secure checking that the PCR primer pair performs an intended function to correctly perform the nucleic acid amplification reaction and that the probe for target nucleic acid performs an intended function.

[28] The testing kit according to any one of [19] through [27] above, including two to 12 of the PCR reaction containers.

Use of the testing kit of the invention of [28] above allows simultaneous and rapid testing of a plurality of target nucleic acids.

[29] The testing kit according to any one of [19] through [28] above, wherein the PCR primer pair is a PCR primer pair to detect herpes simplex virus type 1 (HSV-1) or type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum*, or toxoplasma.

[30] The testing kit according to any one of [19] through [29] above, wherein the plural kinds of PCR primer pair contained in the PCR reaction container include at least any one of combinations below:

(i) HSV-1 detecting primer pair and VZV detecting primer pair;

(ii) HSV-2 detecting primer pair and HHV-6 detecting primer pair;

(iii) EBV detecting primer pair and CMV detecting primer pair; and (vi) HTLV-1 detecting primer pair and *Treponema pallidum* detecting primer pair.

Use of the testing kit of the invention of [29] and [30] above allows simultaneous and rapid detection of pathogens causing infectious uveitis.

[31] The testing kit according to any one of [19] through [30] above, wherein the solid composition for PCR control and the solid composition for PCR reaction contain an oligonucleotide probe labeled with one or more kinds of fluorescent dye to fluorescently detect a PCR amplification product.

[32] The testing kit according to [31] above, wherein the fluorescent dye is at least one selected from the group of FAM (6-carboxyfluorescein), ROX (6-carboxy-X-rhodamine), Cy5 (cyanine-based dye), and HEX (4,7,2',4',5',7'-hexachloro-6-carboxyfluorescein).

Use of the testing kit of the invention of [31] and [32] above allows obtaining a result with higher detection accuracy.

[33] The testing kit according to any one of [19] through [32] above, wherein the solid composition for PCR control and the solid composition for PCR reaction are prepared by freeze drying.

The testing kit of the invention of [33] above simplifies operation for target nucleic acid testing and also simplifies storage before use.

What is claimed is:

1. A method for testing target nucleic acid, comprising:
   mixing a specimen comprising target nucleic acid with positive control nucleic acid to obtain a specimen mixture of the specimen and the positive control nucleic acid;
   mixing the specimen mixture with a PCR buffer solution comprising a surfactant to obtain a buffer solution mixture;
   adding a portion of the buffer mixture to a solid composition for PCR control comprising DNA polymerase, positive control nucleic acid, and PCR reaction control nucleic acid;
   adding a portion of the buffer mixture to a solid composition for PCR reaction comprising DNA polymerase and at least one PCR primer pair; and
   detecting a PCR product generated as a result of the adding of the portion of the buffer mixture to the solid composition for the PCR control and the adding of the portion of the buffer mixture to the solid composition for the PCR reaction.

2. The method according to claim 1, wherein the specimen is aqueous humor of an anterior chamber or a vitreous body.

3. The method according to claim 1, wherein an amount of the specimen is from 12 to 20 µL.

4. The method according to claim 1, wherein the specimen includes at least one pathogen selected from the group consisting of herpes simplex virus type 1 (HSV-1), herpes simplex virus type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum*, and toxoplasma.

5. The method according to claim 1, wherein the positive control nucleic acid in the mixing of the specimen with the positive control nucleic acid is a housekeeping gene.

6. The method according to claim 5, wherein the positive control nucleic acid in the mixing of the specimen with the positive control nucleic acid is TATA-binding protein (TBP).

7. The method according to claim 1, wherein the surfactant in the mixing of the specimen mixture with the PCR buffer solution is a nonionic surfactant.

8. The method according to claim 1, wherein the PCR buffer solution in the mixing of the specimen mixture with the PCR buffer solution is a tris buffer solution comprising KCl, $MgCl_2$, and dNTP mix (a mixture of dATP, dGTP, dCTP, and dTTP).

9. The method according to claim 1, wherein the PCR buffer solution in the mixing of the specimen mixture with the PCR buffer solution includes substances that bond to PCR inhibitors including a negatively charged biologically derived substance and a positively charged biologically derived substance such that PCR inhibitory effect of the negatively charged substance that adsorbs to DNA polymerase and the positively charged substance that adsorbs to DNA is neutralized.

10. The method according to claim 1, wherein at least one of the positive control nucleic acid and the PCR reaction control nucleic acid in the adding of the portion of the buffer mixture to the solid composition for the PCR control is a housekeeping gene.

11. The method according to claim 1, wherein the positive control nucleic acid in the adding of the portion of the buffer mixture to the solid composition for the PCR control is same as the positive control nucleic acid in the mixing of the specimen with the positive control nucleic acid.

12. The method according to claim 1, wherein the positive control nucleic acid in the adding of the portion of the buffer mixture to the solid composition for the PCR control is TATA-binding protein (TBT) and the PCR reaction control nucleic acid in the adding of the portion of the buffer mixture to the solid composition for the PCR control is glyceraldehyde-3-phosphate dehydrogenase (GAPDH).

13. The method according to claim 1, wherein the PCR primer pair in the adding of the portion of the buffer mixture to the solid composition for the PCR reaction is a PCR primer pair to detect herpes simplex virus type 1 (HSV-1) or type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum*, or toxoplasma.

14. The method according to claim 1, wherein the two kinds of PCR primer pair in the adding of the portion of the buffer mixture to the solid composition for the PCR reaction is one of a combination of HSV-1 detecting primer pair and VZV detecting primer pair, a combination of HSV-2 detecting primer pair and HHV-6 detecting primer pair, a combination of EBV detecting primer pair and CMV detecting primer pair, and a combination of HTLV-1 detecting primer pair and *Treponema pallidum* detecting primer pair.

15. The method according to claim 1, wherein the solid composition for PCR control and the solid composition for PCR reaction in the adding of the portion of the buffer mixture to the solid composition for the PCR control and the adding of the portion of the buffer mixture to the solid composition for the PCR reaction includes an oligonucleotide probe labeled with at least one fluorescent dye to fluorescently detect a PCR amplification product.

16. The method according to claim 15, wherein the fluorescent dye is at least one selected from the group consisting of FAM (6-carboxyfluorescein), ROX (6-carboxy-X-rhodamine), Cy5 (cyanine-based dye), and HEX (4,7,2",4",5",7"-hexachloro-6-carboxyfluorescein).

17. The method according to claim 1, wherein the solid composition for PCR control and the solid composition for PCR reaction in the adding of the portion of the buffer mixture to the solid composition for the PCR control and the adding of the portion of the buffer mixture to the solid composition for the PCR reaction are prepared by freeze drying.

18. The method according to claim 1, wherein the detecting of the PCR product is performed by real-time measurement.

19. A kit for testing target nucleic acid, comprising:
a specimen collection container containing positive control nucleic acid;
a PCR reaction solution container containing a PCR buffer solution comprising a surfactant;
a PCR reaction control container containing a solid composition for PCR control comprising DNA polymerase, positive control nucleic acid, and PCR reaction control nucleic acid; and
at least one PCR reaction container containing a solid composition for PCR reaction comprising DNA polymerase and at least one PCR primer pair.

20. The testing kit according to claim 19, wherein the positive control nucleic acid in the specimen collection container is a housekeeping gene.

21. The testing kit according to claim 19, wherein the positive control nucleic acid in the specimen collection container is TATA-binding protein (TBP).

22. The testing kit according to claim 19, wherein the surfactant is a nonionic surfactant.

23. The testing kit according to claim 19, wherein the PCR buffer solution is a tris buffer solution comprising KCl, $MgCl_2$, and dNTP mix (a mixture of dATP, dGTP, dCTP, and dTTP).

24. The testing kit according to claim 19, wherein the PCR buffer solution includes substances that bond to PCR inhibitors including a negatively charged biologically derived substance and a positively charged biologically derived substance such that PCR inhibitory effect of the negatively charged substance that adsorbs to DNA polymerase and the positively charged substance that adsorbs to DNA is neutralized.

25. The testing kit according to claim 19, wherein at least one of the positive control nucleic acid and the PCR reaction control nucleic acid in the PCR reaction control container is a housekeeping gene.

26. The testing kit according to claim 19, wherein the positive control nucleic acid in the PCR reaction control container is same as the positive control nucleic acid in the specimen collection container.

27. The method according to claim 19, wherein the positive control nucleic acid in the PCR reaction control container is TATA-binding protein (TBT), and the PCR reaction control nucleic acid in the PCR reaction control container is glyceraldehyde-3-phosphate dehydrogenase (GAPDH).

28. The testing kit according to claim 19, comprising two to 12 of the PCR reaction containers.

29. The testing kit according to claim 19, wherein the PCR primer pair is a PCR primer pair to detect herpes simplex virus type 1 (HSV-1) or type 2 (HSV-2), varicella zoster virus (VZV), Epstein-Barr virus (EBV), human herpesvirus type 6 (HHV-6), cytomegalovirus (CMV), human T cell leukemia virus type 1 (HTLV-1), *Treponema pallidum*, or toxoplasma.

30. The testing kit according to claim 19, wherein the plural kinds of PCR primer pair in the PCR reaction container include at least one of a combination of HSV-1 detecting primer pair and VZV detecting primer pair, a combination of HSV-2 detecting primer pair and HHV-6 detecting primer pair, a combination of EBV detecting primer pair and CMV detecting primer pair, and a combination of HTLV-1 detecting primer pair and *Treponema pallidum* detecting primer pair.

31. The testing kit according to claim 19, wherein the solid composition for PCR control and the solid composition for PCR reaction include an oligonucleotide probe labeled with one or more kinds of fluorescent dye to fluorescently detect a PCR amplification product.

32. The testing kit according to claim 31, wherein the fluorescent dye is at least one selected from the group consisting of FAM (6-carboxyfluorescein), ROX (6-carboxy-X-rhodamine), Cy5 (cyanine-based dye), and HEX (4,7,2″,4″,5″,7″-hexachloro-6-carboxyfluorescein).

33. The testing kit according to claim 19, wherein the solid composition for PCR control and the solid composition for PCR reaction are prepared by freeze drying.

\* \* \* \* \*